United States Patent
O'Lenick, Jr.

(10) Patent No.: US 6,384,248 B1
(45) Date of Patent: May 7, 2002

(54) MEADOWFOAM BASED SORBITAN ESTERS

(75) Inventor: Anthony J. O'Lenick, Jr., Dacula, GA (US)

(73) Assignee: Fan Tech LTD, Chicago, IL (US)

( * ) Notice: Subject to any disclaimer, the term of this patent is extended or adjusted under 35 U.S.C. 154(b) by 41 days.

(21) Appl. No.: 09/640,265

(22) Filed: Aug. 17, 2000

(51) Int. Cl.$^7$ .............................................. C07D 307/02
(52) U.S. Cl. ...................................................... 549/478
(58) Field of Search ......................................... 549/478

(56) References Cited

U.S. PATENT DOCUMENTS

| | | | | |
|---|---|---|---|---|
| 2,322,820 A | * | 6/1943 | Brown, I | 549/478 X |
| 2,322,821 A | * | 6/1943 | Brown, II | 549/478 X |
| 2,753,303 A | * | 7/1956 | Barker | 549/478 X |
| 3,066,018 A | * | 11/1962 | McGuire | 549/478 X |
| 4,297,290 A | * | 10/1981 | Stockburger | 549/478 |
| 5,178,795 A | * | 1/1993 | Roberts | 549/478 X |
| 5,430,021 A | * | 7/1995 | Ruduic et al. | 514/14 |

FOREIGN PATENT DOCUMENTS

| | | | | |
|---|---|---|---|---|
| WO | 96-16539 | * | 6/1996 | 549/478 |

* cited by examiner

*Primary Examiner*—Floyd D. Higel
*Assistant Examiner*—Ebenezer Sackey

(57) ABSTRACT

The present invention deals with novel emulsifiers. The compounds are esters made by the reaction of sorbitol and meadowfoam acids. The introduction of the unsaturated highly stable meadowfoam acid portion of the molecule into the compounds of the present invention results in improved emulsification efficiency, improved oxidative stability and improved liquidity of the esters.

3 Claims, No Drawings

MEADOWFOAM BASED SORBITAN ESTERS

BACKGROUND OF THE INVENTION

1. Field of the Invention

The present invention deals with novel emulsifiers. The compounds are esters made by the reaction of sorbitol and meadowfoam acids. The introduction of the unsaturated highly stable meadowfoam acid portion of the molecule into the compounds of the present invention results in improved emulsification efficiency, improved oxidative stability and improved liquidity of the esters.

2. Description of the Art Practices

Sorbitan esters have likewise been known for years. U.S. Pat. No. 2,322,821 describes the chemistry.

Generally, unsaturated acids like oleic are used to make emulsifiers. The problem with these materials is that the oleic moiety undergoes a process called rancidity. The rancidity process causes the double bond to oxidize and produce low molecular weight aldehydes. These aldehydes have a bad odor and mal taste at low concentrations. They also polymerize to give dark colored products. The selection of the meadowfoam moiety results in improved color and odor and a heretofore unattainable surfactant.

THE INVENTION

This invention relates to the use of a particular group of exceptionally oxidatively stable meadowfoam acids to prepare sorbitol esters. The esters are made by the reaction of a meadowfoam acid and a sorbitol to make a new series of unexpectedly oxidatively stable emulsifying sorbitan esters.

Esters are a class of compounds which find applications in many diverse segments of the chemical industry. One of the problems which is encountered using non-branched fatty acids to make sorbitol based esters is the fact that the resulting products are dark in color and possess a mal odor. It is very desirable, particularly in cosmetic applications to have products that are light in color and free of bad odors.

The specific structure of the esters of the present invention determines the functional attributes of the product, including odor, color, emulsification and liquidity. There are many possible structural variations which can impact upon the performance of esters. We have learned that the presence of a unsaturated acid side of the molecule results in improved properties.

The unique structure of the meadowfoam results in sorbitan esters with oxidative stability heretofore unattainable. The fatty distribution of the oil ranges from 20 to 22 carbons and has unsaturation in specific locations. The oil contains 97% by weight higher unsaturated alkyl groups. Typically, meadowfoam oil contains 60–65% of a twenty carbon mono-carboxy acid having one unsaturation between carbon 5 and 6. Additionally, it contains 12–20% of a twenty two carbon mono-carboxy acid having one unsaturation between either carbon 5 and 6, or carbon 13 and 14 and 15–28% of a twenty two carbon mono-carboxy acid having one unsaturation between both carbon 5 and 6, or carbon 13 and 14. The combination of the fact that there are 20 to 22 carbon atoms in the group leads to lack of volatility, the presence of unsaturation leads to liquidity and the fact that the di-unsaturated moieties are not conjugated leads to outstanding oxidative stability.

Additional aspects of the invention is the application of these materials as personal care applications were the specific properties of the compound having the unique distribution of the meadowfoam on the other result in superior liquidity, lubricity, and outstanding oxidative stability. The products which result from the oxidative breakdown of unstable products are generally aldehydes. These materials have a mal odor and in addition react with fragrances and preservatives causing formulation problems. This fact makes the products of the present invention all the more important to the formulator of personal care products.

The compounds of the current invention are specific branched esters conforming to the following structure; Sorbitan Mono Meadowfoam Esters

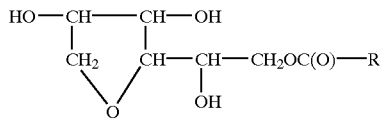

Wherein;
R is derived from meadowfoam and is;
60–65% by weight —$(CH_2)_3$—$CH=CH$—$(CH_2)_{13}$—$CH_3$
12–20% by weight a mixture of
—$(CH_2)_3$—$CH=CH$—$(CH_2)_{15}$—$CH_3$
and
—$(CH_2)_{11}$—$CH=CH$—$(CH_2)_7$—$CH_3$
and
15–28% by weight
—$(CH_2)_3$—$CH=CH$—$(CH_2)_6$—$CH=CH$—$(CH_2)_6$—$CH_3$;

Sorbitan Di meadowfoam Ester

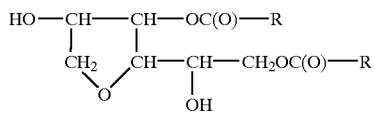

Wherein;
R is derived from meadowfoam and is;
60–65% by weight —$(CH_2)_3$—$CH=CH$—$(CH_2)_{13}$—$CH_3$
12–20% by weight a mixture of
—$(CH_2)_3$—$CH=CH$—$(CH_2)_{15}$—$CH_3$
and
—$(CH_2)_{11}$—$CH=CH$—$(CH_2)_7$—$CH_3$
and
15–28% by weight
—$(CH_2)_3$—$CH=CH$—$(CH_2)_6$—$CH=CH$—$(CH_2)_6$—$CH_3$;

Sorbitan Tri-meadowfoam Ester

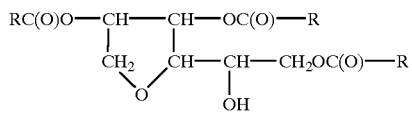

Wherein;
R is derived from meadowfoam and is;
60–65% by weight —$(CH_2)_3$—$CH=CH$—$(CH_2)_{13}$—$CH_3$
12–20% by weight a mixture of
—$(CH_2)_3$—$CH=CH$—$(CH_2)_{15}$—$CH_3$
and
—$(CH_2)_{11}$—$CH=CH$—$(CH_2)_7$—$CH_3$
and
15–28% by weight
—$(CH_2)_3$—$CH=CH$—$(CH_2)_6$—$CH=CH$—$(CH_2)_6$—$CH_3$;

Preferred Embodiment

The preferred embodiments of the present invention are sorbitan mono-meadowfoam esters, sorbitan di-meadowfoam esters, and sorbitan tri-meadowfoam esters.

EXAMPLES

Raw Materials

Meadowfoam Oil

Meadowfoam Oil can be used as a triglyceride, which is the oil as provided, reacted with methanol in processes known to those skilled in the art to make methyl ester, or reacted using technology known in the art to make carboxylic acids. The CAS number of meadowfoam oil is 153065-40-8.

The choice of triglyceride, acid or methyl ester does not change the structure of the resultant ester. It does however change the by-product produced. In the case of the triglyceride, glycerine is produced, in the case of the acid water is produced and in the case of the methyl ester methanol is produced.

Sorbitol

Sorbitol is a six carbon poly-hydroxy compound conforming to the following structure:

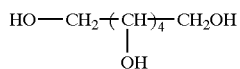

Sorbitol is an item of commerce and is generally sold as a 70% solution in water. The molecule undergoes a reaction under base conditions to cyclize. The optimum cyclization conditions are using KOH at a concentration of between 0.1 and 1.0%. Many ring containing compounds result. Details of the type of compounds produced are outlined in U.S. Pat. No. 2,322,821 incorporated herein by reference. The most simple and most common ring structure is:

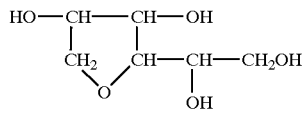

The compound above has four hydroxyl groups present that can be subsequently esterified by the meadowfoam acid. There are three classes of materials that we have made "Sorbitan Mono-meadowfoam Esters" wherein one hydroxyl group is reacted, "Sorbitan Di-Meadowfoam Esters" wherein two hydroxyl groups are reacted, and "Sorbitan Tri-meadowfoam Esters" wherein three hydroxyl groups are reacted. In a subsequent step, the remaining hydroxyl groups are ethoxylated to make a product that is more water soluble.

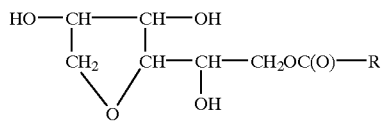

Sorbitan Mono-meadowfoam Ester

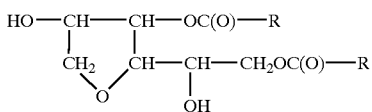

Sorbitan Di-meadowfoam Ester

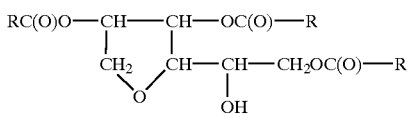

Sorbitan Tri-meadowfoam Ester

Wherein;

R is derived from meadowfoam and is;

60–65% by weight —(CH$_2$)$_3$—CH=CH—(CH$_2$)$_{13}$—CH$_3$

12–20% by weight a mixture of
—(CH$_2$)$_3$—CH=CH—(CH$_2$)$_{15}$—CH$_3$
and
—(CH$_2$)$_{11}$—CH=CH—(CH$_2$)$_7$—CH$_3$
and 15–28% by weight
—(CH$_2$)$_3$—CH=CH—(CH$_2$)$_6$—CH=CH—(CH$_2$)$_6$—CH$_3$;

Sorbitol Cyclization 995.0 grams of 70% sorbitol in water is placed in a round bottom flask equipped with a condenser to remove water, vacuum and agitation. Nitrogen is applied to exclude air and keep the reaction product light in color. 10.0 grams of 45% KOH is then added. The reaction mass is heated to 100–105° C. to remove water. Once the water is removed, the temperature is increased to 180–200 C and one mole of water is distilled off as the material cyclizes.

The resulting product is:

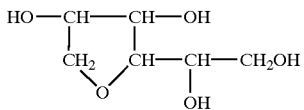

which is used without purification. We refer to this material as sorbitol intermediate. The structure is verified by hydroxyl value, and FTIR.

Ester Synthesis

The esterification reaction is typically carried out using one, two or three equivalents of meadowfoam acid. However, intermediate amounts can be used to make products that are mixtures. For example if 2.5 moles of acid are used, the resulting product will be a mixture of di and tri ester. The esterification reaction can be carried out with or without catalyst, however when no catalyst is used the reaction times are protracted. Catalysts like benzene sulfonic acid, tin, sulfuric acid, tin salts and the like can be used. The most satisfactory catalyst is stannous oxylate.

The ester is prepared by the esterification reaction as shown below:

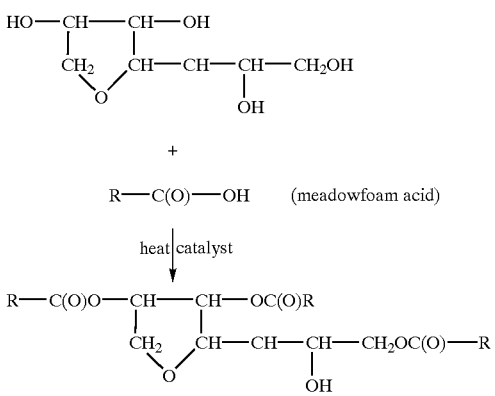

+

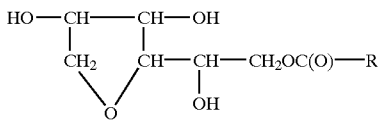   (meadowfoam acid)

heat | catalyst

R—C(O)O—CH—CH—OC(O)R
      |      |
      CH₂   CH—CH—CH—CH₂OC(O)—R
        \\O/         |
                     OH wherein R is derived from meadowfoam and is;
  60–65% by weight —$(CH_2)_3$—CH=CH—$(CH_2)_{13}$—$CH_3$
  12–20% by weight a mixture of
    —$(CH_2)_3$—CH=CH—$(CH_2)_{15}$—$CH_3$
    and
    —$(CH_2)_{11}$—CH=CH—$(CH_2)_7$—$CH_3$
    and
  15–28% by weight
    —$(CH_2)_3$—CH=CH—$(CH_2)_6$—CH=CH—$(CH_2)_6$—$CH_3$;

General Procedure

To 340.0 grams of meadowfoam acid (examples 1–7) is added 165.0 grams of sorbitol intermediate. Next add 0.1% stannous oxylate based upon the total weight of the batch after all ingredients have been charged, under agitation. The temperature of the mass is raised to 180–200° C. and water is stripped off as formed. The acid value and hydroxyl value drop to vanishingly small values, and the saponification value increases to theoretical.

The products are clear liquids and are liquid to extraordinary temperatures. They exhibit outstanding lubrication properties and are outstanding viscosity index modifiers.

Example 1
Sorbitan Mono Meadowfoamate

To 340.0 grams of meadowfoam acid is added to the sorbitol intermediate. Next add 0.1% stannous oxylate based upon the total weight of the batch after all ingredients have been charged, under agitation. The temperature of the mass is raised to 180–200° C. and water is stripped off as formed. The acid value and hydroxyl value drop to vanishingly small values, and the saponification value increases to theoretical.

Example 2
Sorbitan Di-Meadowfoamate

To 680.0 grams of meadowfoam acid is added to the sorbitol intermediate. Next add 0.1% stannous oxylate based upon the total weight of the batch after all ingredients have been charged, under agitation. The temperature of the mass is raised to 180–200° C. and water is stripped off as formed. The acid value and hydroxyl value drop to vanishingly small values, and the saponification value increases to theoretical.

Example 3
Sorbitan Tri-meadowfoamate

To 1,020.0 grams of meadowfoam acid is added to the sorbitol intermediate. Next add 0.1% stannous oxylate based upon the total weight of the batch after all ingredients have been charged, under agitation. The temperature of the mass is raised to 180–200° C. and water is stripped off as formed. The acid value and hydroxyl value drop to vanishingly small values, and the saponification value increases to theoretical.

The compounds of the present invention are liquid esters which are outstanding emulsifiers.

What is claimed is:

1. A sorbitan mono-meadowfoam ester having the following formula:

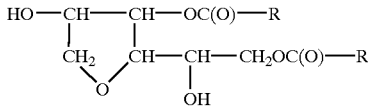

wherein,
  R is;
  60–65% by weight —$(CH_2)_3$—CH=CH—$(CH_2)_{13}$—$CH_3$;
  12–20% by weight a mixture of
    —$(CH_2)_3$—CH=CH—$(CH_2)_{15}$—$CH_3$
    and
    —$(CH_2)_{11}$—CH=CH—$(CH_2)_7$—$CH_3$;
  and
  15–28% by weight
    —$(CH_2)_3$—CH=CH—$(CH_2)_6$—CH=CH—$(CH_2)_6$—$CH_3$.

2. A sorbitan di-meadowfoam ester having the following formula:

HO—CH—CH—OC(O)—R
    |    |
    CH₂  CH—CH—CH₂OC(O)—R
      \\O/      |
                OH

R is;
  60–65% by weight —$(CH_2)_3$—CH=CH—$(CH_2)_{13}$—$CH_3$;
  12–20% by weight a mixture of
    —$(CH_2)_3$—CH=CH—$(CH_2)_{15}$—$CH_3$
    and
    —$(CH_2)_{11}$—CH=CH—$(CH_2)_7$—$CH_3$;
  and
  15–28% by weight
    —$(CH_2)_3$—CH=CH—$(CH_2)_6$—CH=CH—$(CH_2)_6$—$CH_3$.

3. A sorbitan tri-meadowfoam ester having the following formula:

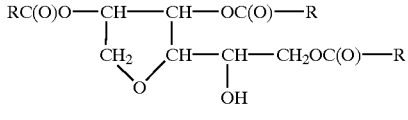

wherein;
  R is;
  60–65% by weight —$(CH_2)_3$—CH=CH—$(CH_2)_{13}$—$CH_3$;
  12–20% by weight a mixture of
    —$(CH_2)_3$—CH=CH—$(CH_2)_{15}$—$CH_3$
    and
    —$(CH_2)_{11}$—CH=CH—$(CH_2)_7$—$CH_3$;
  and
  15–28% by weight of
    —$(CH_2)_3$—CH=CH—$(CH_2)_6$—CH=CH—$(CH_2)_6$—$CH_3$.

* * * * *